(12) United States Patent
Hansen et al.

(10) Patent No.: US 6,251,643 B1
(45) Date of Patent: Jun. 26, 2001

(54) METHOD FOR USING A VEGETABLE BIOMASS AND A SCREW PRESS TO CARRY OUT SAID METHOD

(75) Inventors: Graeme Hansen; Stefan Grass, both of Zürich (CH)

(73) Assignee: 2B AG, Dudendorf (CH)

( * ) Notice: Subject to any disclaimer, the term of this patent is extended or adjusted under 35 U.S.C. 154(b) by 0 days.

(21) Appl. No.: 09/367,437

(22) PCT Filed: Mar. 9, 1998

(86) PCT No.: PCT/CH98/00094

§ 371 Date: Aug. 13, 1999

§ 102(e) Date: Aug. 13, 1999

(87) PCT Pub. No.: WO98/41646

PCT Pub. Date: Sep. 24, 1998

(30) Foreign Application Priority Data

Mar. 18, 1997 (CH) .................................................. 647/97

(51) Int. Cl.⁷ ................ C12P 7/08; C12P 7/10; C12P 19/14; C12P 1/40; A23B 4/03
(52) U.S. Cl. ............... 435/163; 435/163; 435/162; 435/165; 435/99; 435/22; 426/53; 426/69; 426/447; 426/449
(58) Field of Search ..................... 435/161, 162, 435/163, 164, 165, 105, 99, 22; 426/53, 69, 447, 449, 635, 807

(56) References Cited

U.S. PATENT DOCUMENTS

| | | |
|---|---|---|
| 4,302,543 | 11/1981 | Benyaev et al. . |
| 4,321,328 | 3/1982 | Hoge . |
| 4,338,399 * | 7/1982 | Weil et al. . |
| 4,842,877 | 6/1989 | Tyson . |
| 5,559,031 * | 9/1996 | Zinnamosca et al. . |

FOREIGN PATENT DOCUMENTS

| | | |
|---|---|---|
| 29 19 518 | 11/1980 | (DE) . |
| 37 15 953 | 11/1988 | (DE) . |
| 44 23 099 | 3/1995 | (DE) . |
| 0 005 703 | 12/1979 | (EP) . |
| 0 213 023 | 3/1987 | (EP) . |
| 2 550 550 | 2/1985 | (FR) . |
| 58-014995 | 1/1983 | (JP) . |
| WO 82/01483 * | 5/1982 | (WO) . |

* cited by examiner

Primary Examiner—Leon B. Lankford, Jr.
Assistant Examiner—Michele C. Flood
(74) Attorney, Agent, or Firm—Brown Martin Haller & McClain LLP

(57) ABSTRACT

A process and apparatus for recovering organic and inorganic matter from waste material wherein the waste material is sterilized and solid organic matter becomes soft when subjected to heat and pressure. The process may be carried out by first, feeding the waste material into a perforated container (10) mounted within a closed chamber (14). Next, the waste material is agitated and subjected to heat and pressure which sterilizes it and softens the organic matter contained therein. After heating under pressure, the pressure may be suddenly released from the chamber (10) which forces the softened organic matter outwardly through the perforations (12) of the container, thus separating the organic matter from the solid inorganic matter. The softened sterilized, organic matter is then fermented in fermentation chamber (21) to form a mash which may be subjected to further processing in centrifuge (22), distillation column (23) and anaerobic digester (26) to recover fuels such as ethanol and methane, and animal feed supplements.

24 Claims, 1 Drawing Sheet

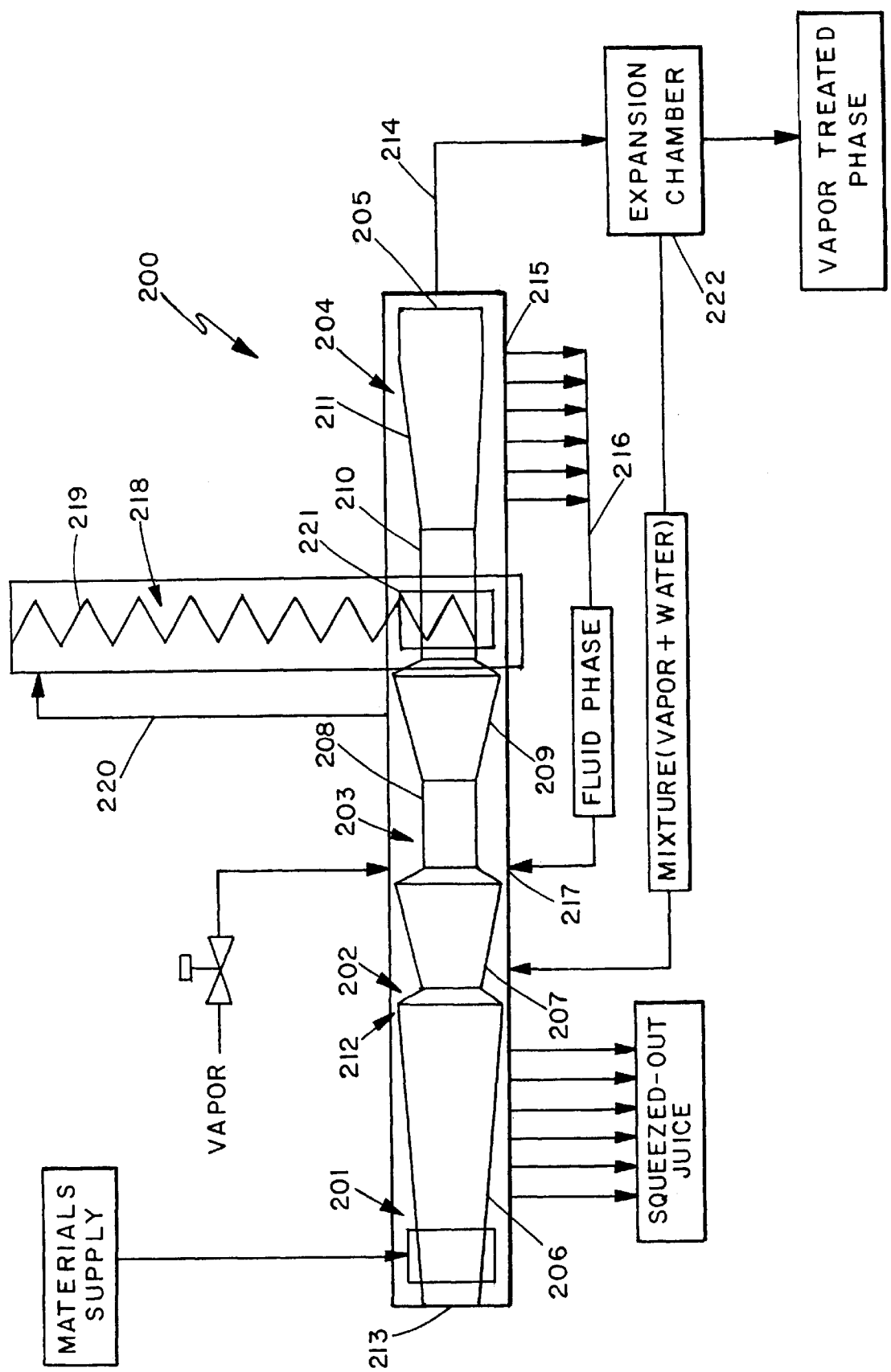

METHOD FOR USING A VEGETABLE BIOMASS AND A SCREW PRESS TO CARRY OUT SAID METHOD

BACKGROUND OF THE INVENTION

The present invention concerns a method of utilizing biomass from agricultural crop essentially in its naturally moist state, as well as a screw press to carry out said method.

Examples of biomass from agricultural crop in its essentially naturally moist state that can be taken into consideration are plants or parts of plants with especially high protein content and/or sugar content, their derivatives and residues. This applies in particular to clover, alfalfa and grass, but also to bean plants, soybean, sorghum, mustard, collard greens, turnips, banana leaves, bagass, grape skins, husks/skins, residue of fruit such as residue of citrus fruits and pitted fruit, and also rampant water plants such as duck-weed and water hyacinth, and several others of that nature. In connection with the use of biomass, individual steps like shredding, extruding, hydrolysis, cooling, decomposition by enzymes, decomposition by microorganisms, anaerobic decomposition, recovery of fermentation gases, discharge of various phases essentially like fluid phases, phases of low solids content, phases of high solids content, or gas-type phases etc., are already known per se, as well as the individual utilization of separated phases as a feed, a fertilizer, for the production of ethanol, for the production of carbon dioxide, as a fuel, etc. In screw presses it is also known to form sealing plugs of the treated material for the purpose of separating various chamber areas from one another.

However, this prior art is not known as a whole in the form of a single integrated system. In detail this means: WO-82/01483 discloses a method of utilizing of a mixture of organic and inorganic material in municipal waste, as well as a device for the continuous operation of this method. The material is provided in chopped form; then follows a sterilization treatment of the entire waste material by means of pressurized vapor; subsequently the pressure is released and the vapor-treated waste material is separated into a phase of high organic materials content that is capable of flowing and a phase of high inorganic solids content; then follows a decomposition of organic materials in the phase capable of flowing, by the action of enzymes and/or by fermentation through microorganisms, and the decomposed phase is separated into solids and fluid; the fluid is distilled and the residue is again separated into solids and fluid; the latterfluid is fermented under anaerobic conditions and the gas phase that develops during this process is separated in view of being utilized; the fluid from the fermentation and the solids in the residue of the distillation are also utilized.

With this method according to WO-82/01483, the waste material is only subjected to pressure, however, it will not be simultaneously compressed (pressed and compacted) and hence, it remains voluminous and maintains its moisture.

Also, the separation of organic and inorganic contents takes place only after the pressure treatment.

In addition, there is an irreversible expansion of the vapor phase after which the energy of the vapor cannot be recovered and recycled to the process because it is lost in the condensed water.

Moreover, a very first method step is the sterilization of the material in its still voluminous loose shape, which may be appropriate when the method is applied to municipal waste, since such waste endangers the environment. To apply this method to biomass from agricultural crop is not optimal, since such biomass does not endanger the environment and therefore it is not urgent to sterilize it while in its still voluminous state. However, the sterilization cannot be delayed when the method of WO-82/01483 is performed, since it takes place spontaneously together with the pressurized vapor treatment as a step that imperatively occurs prior to the release of pressure.

In general the method according to WO-82/01483 is directed to first separate the organic and inorganic materials contents and only then initiate their utilization, whereas such separation is not appropriate at all to biomass from agricultural crops.

Thus, the method according to WO-82/01483 is not capable of providing economically optimal results with biomass from agricultural crop essentially in its naturally moist state.

DE-4423099 discloses a method of utilizing biomass from agricultural crop as well as a screw press to perform the method. The chopped biomass is compressed in a screw press and separated into a phase of low solids content and a phase of high solids content; the phase of low solids content is separated; then a fermentation is performed that is not described any further. This method is suited for the production of fermentation gas, however, it is not suitable for the production of high-grade products like ethanol, protein concentrate and fibers. There takes place no vapor treatment nor expansion nor cooling of the starting material.

U.S. Pat. No. 4,302,543 discloses a method of utilizing biomass from agricultural crop. The chopped biomass is compressed in an extruder under high pressure and high temperature without any prior separation of solids and fluid; after sufficient cooling, the substance is hydrolyzed by the action of enzymes. This method was developed for the utilization of raw materials having a high content of starch such as corn, wheat, rice, barley, rye and oats, however, it does not allow for the processing of raw materials that primarily contain cellulose, for the production of ethanol, protein concentrate and fibers. Also, there takes place no compression of the material to separate solids and fluid and no recovery of vapor at the end of the heat treatment. A release of the pressure applied to the material kept at high temperature and under high pressure is said in the description to be known prior art.

U.S. Pat. No. 4,842,877 discloses an essentially chemical method for the processing of biomass from agricultural crop by the decomposition of wood fibers (lignocellulose) to become a feed supplement. The first step of this method is an alkaline hydrolysis at somewhat elevated temperature. The fluid phase obtained is mixed with a chelating agent. Among other chemical method steps an oxidation with hydrogen peroxide and oxygen takes place in an extruder.

JP-58-014995 (as can be read in Patent Abstracts of Japan) discloses the improvement of a fermentation method by means of prior removal of ballast fibers that are not capable of fermentation. The material to be fermented is compressed in a screw press and simultaneously separated into two phases; the phase of high solids content is separated; then the phase of low solids content is fermented, the fermentation gas that develops during this process is separated and utilized, the remaining mixture phase that is capable of flowing is in its turn separated into two phases, and both phases will be utilized. There is no vapor treatment, no cooling and no addition of enzymes and/or yeast that would be required for the production of ethanol and by-products.

DE-2919518 discloses a method of utilizing biomass from agricultural crop essentially in its naturally moist state, as well as a screw press to carry out said method. The chopped biomass is treated with pressurized vapor; after cooling down, a fermentation with microorganisms takes place, optionally with addition of yeast, and only then a separation of the mixture into two phases takes place in the screw press and these phases are processed. This method was developed to obtain ethanol from free sugar contained in sugar cane and is not suitable to produce ethanol from cellulose. In addition, no enzymes are used for the cleavage of the fibers contained in the raw materials.

U.S. Pat. No. 4,321,328 discloses a method for the recycling of ethanol containing liquor, which may be applied to the production of ethanol from raw materials containing cellulose. In this method the raw material is suspended by means of recycled ethanol containing liquor and then mechanically disintegrated, hydrolyzed by the action of enzymes and fermented with microorganisms. Seizure, conditioning and pre-treatment of the raw materials are not further described.

EP-0005703 discloses a method for the utilization of solid household waste and biomass. In the case of processing household waste, various substances contained therein are first separated from one another in several steps. Then, all raw materials are subjected to a grinding of the contained substances that are capable of being hydrolyzed, a sterilization and a saccharification by means of sulfurous acid, a neutralization, a fermentation, a separation of the solids and fluid, and a distillation of the fluid phase.

EP-0213023 discloses a method of producing ethanol and gluten from grain.

FR-2550550 discloses a method for the processing of biomass from agricultural crop. The first step of this method is a hydrolysis at high temperature and under high pressure; this is followed by a release of pressure in the course of which the material is separated into a fluid phase and a solid phase; the lignin is removed from the solid phase by means of a solvent; then, a hydrolysis again takes place at high temperature and under high-pressure; if necessary, a saccharification by the action of enzymes will follow. The object of this method is the liquefaction and separation of hemicellulose, cellulose and lignin.

DE-3715953 discloses a method for the processing of materials containing cellulose such as waste containing paper, straw and wood waste, as well as a screw press for performing the method. Following the chopping of the mass, a dissolution and a sterilization take place in the screw press through an increase in temperature and pressure, then a completion step follows in a closed system with a discharge of oxygen, and the product thereof is then further processed. There is no treatment of the raw materials with vapor.

The aforementioned prior art does not lead to any obvious combination of prior art techniques that would allow to avoid the aforementioned disadvantages that arise when the method of WO-82/01483 is performed.

More particularly, using this prior art did not allow up to now to obtain any economically acceptable implementation of the separate method steps into an optimally operated integrated system. This could be attributed to several reasons:

Where raw materials containing sugar or starch are processed, the cost of the raw materials in comparison to the price for ethanol is in general too high.

Where methane gas (fermentation gas) is produced the low price of the product merely allows to apply the method to raw materials, the disposal of which is compulsory. On the other hand, economical utilization of raw materials from agricultural crops is not possible.

Where ethanol is produced exclusively, the benefits are too low, compared to the expensive processing of a high-tech method. This supports the economic pressure to establish installations with a very large processing capacity. High development costs, as well as high transportation costs for raw materials, must be included in the calculation for such large installations.

SUMMARY OF THE INVENTION

Accordingly, it is an object of the invention to suggest a method of utilizing biomass from agricultural crop essentially in its naturally moist state, where the economical aspect of the turnover of energy, input and output materials can be optimized overall and moreover, optimally adapted to allow for the seasonal fluctuations of the quantities and values.

More particularly, it is an object of the invention to achieve through a method of the kind mentioned above:

Utilization of various substances contained in the biomass;

Linking, within the method itself, the requirements regarding the treatment and storage of raw materials with the requirements regarding the utilization of the contained substances;

Optimal further processing and utilization of the separated essentially fluid or solid phases; and Optimizing the overall energy balance of not only the individual method steps but of the method as a whole.

To attain these objects, according to the invention a method of utilizing biomass from agricultural crop in its naturally moist state is characterized by the following combination of successive method steps:

(a) Providing the biomass in a chopped form appropriate to processing in screw presses;

(b) Pressing the provided biomass from method step (a) and concomitant separation of the pressed biomass into each of a phase of low solids content and a phase of high solids content, and separation of the phase of low solids content for the latter's utilization;

(c) Processing the phase of high solids content from method step (b) with pressurized vapor;

(d) Releasing pressure of the pressurization built-up at method step (c) and concomitant separation of the vapor-treated phase from method step (c) into each of a vapor phase and a phase of high solids content, and separation of the vapor phase for the latter's utilization;

(e) Cooling the phase of high solids content from method step (d) and concomitant utilization of heat recovered in this step;

(f) Decomposition of materials in the cooled phase from method step (d) by the action of enzymes and/or by fermentation with microorganisms and concomitant separation of the decomposed phase into each of a gaseous phase and a phase capable of flowing, and separation of the gaseous phase for the latter's utilization;

(g) Separation of the phase capable of flowing from method step (f) into each of a phase of low solids content and a phase of high solids content, and separation of the phase of high solids content for the latter's utilization;

(h) Utilization of the phase of low solids content from at least one of the method steps (b) and (g).

A screw press for the performing the method according to the invention is characterized by a screw press for continuously performing the method, characterized by chamber regions for the respective carrying out of stages of pressing and treating material each time provided thereto with an aqueous fluid phase essentially devoid of solids, whereby the chamber regions are axially disposed in line with at least one common integral shaft having screws arranged thereon for conveyance of material and are, during the operation of the screw press, sealed off from each other by a plug of compressed material, and essentially on and along one of the chamber regions there is provided a recycling of the aqueous fluid phase in a direction opposite to that of the conveyance of material.

The method according to the invention is particularly well-suited for use with biomass having a moisture content of about 65 to 90 percent by weight and a protein content of about 10 to 30 percent by weight, relative to the dry substance.

With the method of the invention, the following will be achieved:

The processing of raw materials with a high protein content makes possible the production of protein concentrate and yeast as by-products, which increases the benefit of the method as a whole and at the same time significantly contributes to enhance its efficiency. This way, facilities with a rather small capacity may be operated economically, which makes the utilization of existing infrastructures possible and keeps the energy consuming transport of raw materials within limits, which in turn reduces the costs. On the other hand, the additional cost of the facilities for obtaining the production and the quality assurance of the by-products is relatively low, compared to the overall facility costs.

The raw materials taken into consideration are available throughout a rather long period of time and can be processed as fresh material, which eliminates the cost of drying, loss during storage, the need for storage space and the cost of storage. In the processing of clover and grass, for example, operation during the winter may be assured by delivering additional raw materials to the facility during the summer, compressing this material there, and immediately processing the additional squeezed-out fluid with its perishable substances sugar and proteins together with the fluid squeezed out during the normal summer production, whereas the residue that has a high fiber content will be ensiled with the addition of lactic acid bacteria. This allows for compact storage with a high storage density, which minimizes the storage losses and eliminates drying costs.

The method operation according to the invention regarding extrusion and pre-treatment of raw materials leads to a significant reduction in the amount of vapor necessary for the vapor treatment.

The handling of the pre-treated fibers according to the invention increases the operation safety and brings still further processing advantages.

The compression of the vapor treated phase according to the invention makes possible the recovery of fluid that consists of pressurized condensate and reduces the loss of energy due to the release of pressure. Whereas the temperature of the vapor is only 100° C. during the release of pressure, the temperature of said fluid, prior to the release of pressure, is exactly the temperature that has been set as the operating temperature. Said fluid can advantageously be used to pre-heat the raw materials.

The separated phase of low solids content, optionally combined, may be used as a fermentation medium after having been hygienized. The protein contained therein may also be coagulated, separated and utilized. In addition, valuable ingredients like limonens from residues of citrus processing, tannins from residues of cider manufacturing etc., may be contained therein, depending on the raw materials being used, and may be separated and utilized. This further processing and utilization will considerably increase the optimization of the economic value of the method according to the invention.

In the phases of low solids content that have been separated, the content of sugars capable of fermentation varies largely, depending on the raw material and the season, and these variations may be evened out by co-processing added washed sugar beets. In this manner the value of the phases of low solids content may be increased, and their utilization as a fermentation medium may be stabilized. At the same time the pressing residue of the sugar beets can be further processed in combination with the phase of high solids content. Overall, this lead to an adaptation of the method to the corresponding seasonal fluctuations in amount and value.

The preferred cooling, according to the invention, of the vapor-treated phase of high solids content by means of direct contact with the cooling fluid in two consecutive cooling stages is capable of attaining the following objects:

The facility may be built more compact and thus, more cost-effective than with the use of indirect cooling for which a large cooling exchange surface would be required, due to poor heat transfer.

With the two cooling stages and the intermediate stage provided in between it becomes possible to raise the phase of high solids content to a temperature which is optimal regarding the enzymes and microorganisms used and to provide addition of the latter exactly under these conditions, for example at the known optimal temperature of the enzymatic saccharification of 40–65° C. In addition, it is advantageous that the enzymes are added to freshly pre-treated fibers, instead of the reaction mixture in the fermentation unit.

With the two cooling stages and the intermediate stage provided in between it becomes possible to make different operating conditions compatible with one another. Through proper dimensioning and modification of the intermediate stage it is possible, for example, to connect with each other a pre-treatment that takes place during 8–16 hours per day and a continuous further processing.

Due to the closed circuit of the cooling fluid, no enzymes are lost.

The screw press according to the invention makes it possible to achieve that the material conveyance loop formed by the additional chamber region connecting the two partial regions with one another will allow to independently adjust the stay time of the phase of high solids content under pressure and temperature conditions that can optionally be selected independently of each other.

BRIEF DESCRIPTION OF THE DRAWINGS

The present invention will be better understood from the following detailed description of a preferred embodiment of the invention, taken in conjunction with the accompanying drawings in which:

FIG. 1 is a schematic representation of a screw press for performing the method of the invention.

DESCRIPTION OF THE PREFERRED EMBODIMENT

Freshly cut clover and grass with a dry material content of 15–30 percent by weight and typically of about 20 percent by weight is delivered for 8–16 hours per day and fed via a conveying and proportioning screw to a macerator that turns the raw material into a flowing paste.

In the screw press, a juice is squeezed out from this flowing paste (squeezed-out juice), which juice contains large amounts of sugar capable of fermentation as well as raw protein.

This juice is subjected to heat treatment with vapor in a heat exchanger, whereby the proteins are coagulated. By doing this the juice also is hygienized, which makes it usable as a fermentation medium. Preferred utilizations are the separation and further processing of the proteins contained in the juice, together with the utilization of the sugars capable of fermentation as a carbon source for microorganisms. It is also possible to transfer the hygienized juice into one or more fermenters that contain the phase of high solids content, in combination with a later separation and processing of the proteins contained in the juice together with the fully fermented flowing paste of high protein content.

The phase of high solids content that is left over at about 30–60° C. after the squeezing out is first pre-heated to about 80° C. by means of recycled fluid (mixture of vapor and water at about 100° C.) and then fed further into a pressure chamber where it is subjected to vapor treatment at about 100–170° C. and typically at about 140° C. under about 4 bar for about 10 minutes by means of the addition of vapor (preferably under 10 bar) and a hot aqueous phase.

Immediately afterwards hot fluid is squeezed out from this vapor-treated phase and generally put to use, typically being recycled to the beginning of the same vapor treatment where it is utilized as a hot aqueous phase.

The remaining vapor-treated phase of high solids content is moved from the press to an expansion container where its pressure is released and its temperature is brought to 100° C. By means of this release of pressure the phase of high solids content is made loose, which makes it easy to be transported and subjected to additional processing. The fluid resulting from the release of pressure (mixture of vapor and water at about 100° C.) is reused as recycled fluid in the pre-heating mentioned above.

Immediately afterwards, the remaining vapor-treated phase of high solids content is cooled down. This cooling proceeds in two stages, and an intermediate chamber is arranged between the two cooling stages. In each of the cooling stages the cooling fluid and the phase of high solids content are mixed, and the resulting mixture is subsequently separated by pressing into a cooling fluid and a phase of high solids content.

In the intermediate chamber the phase of high solids content is supplied with enzymes, typically cellulases, that can develop their optimal action at the temperature values of about 40–70° C. and typically about 50° C. prevailing there. At the same time this intermediate chamber serves as a buffer to balance the above-described treatment, which takes place in periods of 8 to 16 hours per day, with the following continuous treatment that will be now be described. From the intermediate chamber the transfer proceeds to a second cooling stage, in which the phase of high solids content is cooled to about 30° C. From this second cooling stage, the charging of fermentation units is accomplished by means of a feed screw.

The major part of the cooled material to be processed is transferred to one or more main fermentation units for simultaneous saccharification and fermentation. A minor part of the material remaining in the intermediate chamber, typically about 5–10 percent by weight of the amount to be processed, is sent to a separate auxiliary fermentation unit for enzyme production. There, the enzyme production proceeds under conditions appropriate therefor, mainly with the help of fungi strains of the genus trichoderma or aspergillus. The enzyme-containing stock juice fully fermented in the auxiliary fermentation unit, including the mycelium contained therein, is then transferred to the main fermentation unit.

In the main fermentation unit there takes place, typically at a temperature of 35° C., a chemical reaction of the fibers contained in the phase of high solids content to produce ethanol. In the course of this reaction carbon dioxide is released, which is collected, compressed and brought to market in a liquefied form.

The stock juice fully fermented in the main fermentation unit contains water-soluble materials and solids that can be separated using a decanter and/or further appropriate filters. The separated solids can be utilized, in fluid or dehydrated form, as animal feed. The fluid phase containing the water-soluble materials is transferred for extraction of ethanol to a distillation column that receives its necessary heat from vapor.

After distillation at about 100° C. the fluid phase from which ethanol has been removed mainly contains sugars not capable of fermentation such as xylose and arabinose, and organic acids as well as nutrient salts. The organic material contained in the fluid phase is reacted in a digestion chamber, typically at a temperature of 37° C., to produce fermentation gas that is utilized to provide heat and can cover almost the entire need for processing heat. Warm water, which is produced by the corresponding cooling of the organic material from about 100° C. to about 37° C., is also made available and utilized as described above.

Additionally, the production of fermentation gas performs to a large degree a purification of the processing water, which makes the latter re-usable.

According to the above-described procedure, a metric ton of dry material of the above-mentioned raw material allows to prepare or collect about 180–250 liters of ethanol (with about 95 percent purity), 150–300 kg of protein concentrate (having about 90 percent by weight dry material and about 35–50 percent by weight raw protein), 150–300 kg of fibers and 140–200 kg of carbon dioxide. With the likewise possible production of yeast, a metric ton of dry material of the above-mentioned raw material allows to prepare or collect about 110–180 kg yeast (with about 30 percent by weight dry material), 90–160 liters ethanol (with about 95 percent purity), 150–300 kg of protein concentrate (with about 90 percent by weight dry material and about 35–50 percent by weight raw protein), 150–300 kg of fibers and 50–100 kg of carbon dioxide.

According to market conditions it is also possible to partially or completely shift away from ethanol production so as to favor a maximization of the yeast or fiber production. Under such conditions, about 180–350 kg yeast (with about 30 percent by weight dry material) or 300–400 kg of fibers can be produced per metric ton of dry material of the above-mentioned raw material.

The above-described procedure also offers as further options the production of other products, for example citric acid or acetic acid (by using microorganisms appropriate to that effect), other decomposition products (by using enzymes appropriate to that effect such as amylases, pectinases, and/or hemicellulases), xylite and/or furfural (by further processing of the xylose contained in the fully fermented fermentation stock juice), etc. In particular, cellulosic material can be produced by carrying out the vapor treatment of the phase of high solids content remaining after the pressing at about 30–60° C. at a lower temperature and in a shorter time than would be necessary in order to obtain, through the subsequent action of enzymes and/or microorganisms, the best possible saccharification. In this manner, at the end of the decomposition there remain, in this phase of high solids content, water-insoluble polysaccharides that represent cellulosic material.

In the following description of a screw press for carrying out the described method, reference is made to the schematic representation of such a screw press that is provided in FIG. 1.

The screw press designated as a whole with 200 includes chambers 201,202,203,204, each of which is destined to carry out, on material each time provided thereto, method steps of pressing and of treatment with an aqueous fluid phase essentially devoid of solids.

The chambers 201,202,203,204 are axially disposed in line next to each other with a common integral shaft 205. On this shaft 205, screws 206,207,208,209,210,211 are arranged for conveyance of material into the respective chamber. It is to be understood that it is possible, in known manner, to provide in these chambers several integral shafts with respective screws, for example each time two parallel, opposite-turning shafts with corresponding screws.

During the operation of the screw press, there is formed at the exit end of each screw a plug of compacted material (for example in chamber 201 at 212 on the exit end of screw 206). This plug seals off the chamber in question (in this exemplary case: 201) from the next chamber (in this case: 202), but does not prevent the conveyed material, pressed to constitute a plug, from being pressed out of the chamber at this location and in this manner to be advanced from one chamber to the next.

At the entrance end of the first chamber 201, the material to be processed is conveyed-in, whereby no plug forms there and the closure of chamber 201 must be provided by means of a wall 213.

The processed material exits from the last chamber 204 in that the plug is pressed out into a line 214, as is schematically indicated in the drawing.

The pressing of the processed material in the last chamber 204 makes it possible to extract the fluid and/or gaseous part of the processed material out of this chamber 204 through openings 215 without causing a drop in temperature, collect it in a line 216, and return it through this line 216 along the chambers 204,203 and into chamber 203 at an opening 217. This builds up a recycling of the aqueous fluid phase extracted from the processed material essentially along a chamber region encompassing chambers 203,204 in a direction opposite to that of the conveyance of material.

This chamber region that encompasses chambers 203,204 is divided into two sub-regions disposed in line next to each other, of which the one includes the chamber 203 with the screws 208,209 and the other includes the chamber 204 with the screws 210,211. All of these screws are formed as sections of the common integral shaft 205, and they provide for the conveyance of material into the respective chambers.

During operation of the screw press there is also formed between the two said sub-areas, i.e. between the chambers 203 and 204, from the material that is pressed and conveyed at this location, a plug that seals chamber 203 from the next chamber 204. However, at this interface between the chambers 203 and 204 the screw press is constructed in such manner that the plug created there hinders the conveyed material from passing directly from chamber 203 to chamber 204 i.e. from the exit end of the screw 209 to the entrance end of screw 210. This is because at that location it is desired that the conveyed material pass through a loop between the chambers 203 and 204 i.e. between the aforementioned sub-regions, which loop links the chambers 203 and 204 with each other.

This loop includes a (schematically represented) chamber 218 that has its own screw 219 (schematically represented) for conveyance of material as well as a corresponding duct 220 (schematically represented) for feeding the material to be processed from the exit end of screw 209 to the entrance end of chamber 218, and also a corresponding duct 221 (schematically represented as an opening) for feeding the material processed in chamber 218 from the exit end of screw 219 to the entrance end of chamber region 204.

In this loop the conveyance speed and hence, the stay time of the conveyed material can be set in an manner that is independent of the conditions prevailing in the chambers 201,202,203,204 i.e. at the screws 206,207,208,209,210, 211. In this manner, for example, (and with the help of a loop of corresponding length) a rather long period of time where the material stays in the loop can be achieved also with a rather high conveyance speed at the shaft 205.

From the screw press 200, the phase of high solids content that has now been vapor-treated passes to an expansion chamber 222 that is connected downstream of the screw press 200 i.e. the chamber 204, where its pressure is reduced, it is brought to a temperature of 100° C. and it is simultaneously loosened. For the fluid that results from the release of pressure (a mixture of vapor and water at about 100° C. ) a recycling to chamber 202 of the screw press 200 is provided in the region of the exit end of the corresponding screw 207, and is shown schematically in the drawing.

It will be recognized that there are numerous embodiments of the present invention which, while not expressly described above, are clearly within the scope and spirit of the invention. The above description is therefore intended to be exemplary only, and the scope of the invention is to be limited solely by the appended claims.

We claim:

1. Process for the utilization of biomass from agricultural crop in a naturally moist state, the comprising the steps of:
   (a) preparation of the biomass in a chopped form for processing in screw presses;
   (b) pressing of the prepared biomass from step (a) and concomitant separation of the pressed biomass into each of a high-solid phase of high solids content and a low-solid phase of low solids content for the latter's utilization;
   (c) processing of the high-solid phase from step (b) with pressurized vapor;
   (d) releasing pressure of the pressurization built up at step (c) and concomitant separation of the vapor-treated phase from step (c) into a vapor phase and a high-solid phase of high solids content, and separation of the vapor phase for the latter's utilization;
   (e) cooling of the high-solid phase from step (d) under utilization of the heat recovered in this step;
   (f) decomposition of materials in the cooled phase from step (d) by the action of enzymes and/or through fermentation with microorganisms and concomitant separation of the decomposed phase into a gaseous phase and a phase capable of flowing, and separation of the gaseous phase for the latter's utilization;
   (g) separation of the phase capable of flowing from step (f) into a high-solid phase of high solids content and a low-solid phase of low solids content, and separation of the high-solid phase for the latter's utilization; and
   (h) utilization of the low-solid phase from at least one of the steps (b) and (g).

2. Process according to claim 1, characterized in that, immediately following the vapor treatment of step (c), there is performed a pressing of the vapor phase from step (c) and a concomitant separation of the pressed phase into an aqueous fluid phase essentially devoid of solids and a high-solid phase of high solids content, before the release of pressure in step (d) takes place, whereby the aqueous fluid phase is separated out and recycled to step (c).

3. Process according to claim 1, further comprising that the cooling of the high-solid phase in procedural step (e) proceeds in two stages, whereby the high-solid phase undergoes an interim stage between the two cooling stages, and through this process at least one enzyme, that is decomposed from procedural step (f), is added to the high-solid phase.

4. Process according to claim 1, further comprising that the decomposition of materials from procedural step (f) includes an alcoholic fermentation and that the low-solid phase from procedural step (g) undergoes a distillation for the separating out of ethanol.

5. Process according to claim 1, further comprising that the decomposition of materials from procedural step (f) includes an effect from sugar-producing enzymes like cellulose, amylase, pectinase and/or hemicellulase.

6. Process according to claim 5, further comprising that the vapor treatment in procedural step (c) will be carried out at a lower temperature and/or with a shorter time period so that a best possible Saccharification through the effect of sugar-producing enzymes and/or microorganisms from procedural step is available, so that after successful decomposition, non-soluble polysaccharide fibers remain, that can be separated out from the decomposed phase as cellular material.

7. Process according to claim 1, further comprising that the recovered vapor from procedural step (d) is applied to a pre-heating the warming of the high-solid phase from procedural step (c).

8. Process according to claim 1, further comprising that the low-solid phase from procedural step (b) and/or (g) undergoes an anaerobic decomposition and concomitant separation of the decomposed phase into fermentation gas and a fluid phase, that separates out fermentation gas, part of which will be used as fuel.

9. A screw press for continuously performing the process according to claim 2, comprising chamber areas for the respective carrying out of stages of pressing and treating material each time provided thereto with an aqueous fluid phase essentially devoid of solids, whereby the chamber areas are axially disposed inline, with at least one common integral shaft with respective screws arranged thereon for conveyance of material and during operation of the screw press are sealed off from one another by a plug of compressed material, and basically on and along one of the chamber areas there is provided a recycling of the aqueous fluid phase in a direction opposite to that of the conveyance of material.

10. A screw press according to claim 9, further comprising that the chamber area provided with the recycling is divided into two axial inline sub-area, each sub-area with a screw constructed as part of the common integral shaft for the conveyance of material, both of the sub-areas during the operation of the screw press are sealed off from each other by a plug of compressed material and, between both sub-areas, an additional chamber area is located with its own separated screw for the conveyance of material, the additional chamber area linking the two sub-areas and forming in between, a material conveyance loop.

11. Process according to claim 1 further comprising producing protein concentrates thereby.

12. Process according to claim 1 further comprising extraction of ethanol as well as production of protein concentrate and of fibers thereby.

13. Process according to claim 1 further comprising extraction of ethanol as well as production of protein concentrate and of fibers thereby essentially out of existing grass biomass.

14. Process according to claim 2, further comprising that the cooling of the high-solid phase in procedural step (e) proceeds in two stages, whereby the high-solid phase undergoes an interim stage between the two cooling stages, and through this process at least one enzyme, that is decomposed from procedural step (f), is added to the high-solid phase.

15. Process according to claim 2, further comprising that the decomposition of materials from procedural step (f) includes an alcoholic fermentation and that the low-solid phase from procedural step (g) undergoes a distillation for the separating out of ethanol.

16. Process according to claim 2, further comprising that decomposition of materials from procedural step (f) includes an effect from sugar-producing enzymes like cellulose, amylase, pectinase and/or hemicellulase.

17. Process according to claim 16, further comprising that the vapor treatment in procedural step (c) will be carried out at a lower temperature and/or with a shorter time period so that a best possible sweeting through the effect of sugar-producing enzymes and/or microorganism from procedural step is available, so that after successful decomposition, non-soluble polysaccharide fibers remain, that can be separated out from the decomposed phase as cellular material.

18. Process according to claim 2, further comprising that the recovered vapor from procedural step (d) is applied to the warming of the high-solid phase from procedural step (c).

19. Process according to claim 2, further comprising that the low-phase from procedural step (b) and/or (g) undergoes an anerobic decay under separation of the decaying phase into fermentation gas a fluid phase, that separates out fermentation gas, part of which be used as fuel.

20. Screw press means for the continued advancement of the process according to claim 1, identified by chamber areas for the respective carrying out of stages of pressing and processing through a non-solid aqueous fluid phase of respective advancing materials, whereby the chamber areas axially dispose inline, with at least one common integral shaft with respective screws meant for material advancement and during the operation of the screw press means sealed off from each other by a plug of compressed material, and basically on and along one of the chamber areas, a backward movement of the aqueaous fluid phase in the opposite direction of said material is foreseen.

21. Screw press means according to claim 20, further comprising that the chamber area foreseen with the backward movement is divided into axial inline sub-areas, each sub-area with a screw constructed as part of the common integral shaft is foreseen for the material advancement, both of the sub-areas during the operation of the screw press means are sealed off from each other by a plug of compressed materials and, between both sub-areas, an additional chamber area with its own separate screw for the expected material advancement is foreseen, that links the two sub-areas and forms in between, a loop with the material advancement.

22. Process according to claim 2 further comprising producing protein concentrates thereby.

23. Process according to claim 2 further comprising extraction of ethanol as well as production of protein concentrate and of fibers thereby.

24. Process according to claim 2 further comprising extraction of ethanol as well as production of protein concentrate and of fibers thereby essentially out of existing grass biomass.

* * * * *